(12) United States Patent
Moessler et al.

(10) Patent No.: US 7,148,192 B2
(45) Date of Patent: Dec. 12, 2006

(54) NEUROPROTECTIVE DIETARY SUPPLEMENT

(75) Inventors: Herbert Moessler, Seekirchen (AT); Christa Riedl, Unterach (AT); Wolfgang Schmitzberger, Mondsee (AT); Heinz Schnait, Seewalchen (AT)

(73) Assignee: Ebwe Pharma Ges. M.H. Nfg.KG, Unterach (AT)

( * ) Notice: Subject to any disclaimer, the term of this patent is extended or adjusted under 35 U.S.C. 154(b) by 60 days.

(21) Appl. No.: 10/766,480

(22) Filed: Jan. 29, 2004

(65) Prior Publication Data

US 2005/0227922 A1 Oct. 13, 2005

(51) Int. Cl.
*A61K 38/00* (2006.01)
*A61K 38/02* (2006.01)
*A61K 38/16* (2006.01)
*A61K 38/08* (2006.01)

(52) U.S. Cl. ................................ 514/2; 514/13; 514/16
(58) Field of Classification Search ...................... None
See application file for complete search history.

(56) References Cited

U.S. PATENT DOCUMENTS

| | | | |
|---|---|---|---|
| 5,759,991 A | 6/1998 | Tohdoh | |
| 5,977,311 A * | 11/1999 | Nandabalan et al. | 530/358 |
| 5,985,339 A * | 11/1999 | Kamarei | 426/72 |
| 6,140,116 A | 10/2000 | Dinsmore | |
| 6,174,862 B1 | 1/2001 | Brenneman | |
| 6,214,349 B1 * | 4/2001 | Segelman | 424/738 |
| 6,225,444 B1 | 5/2001 | Shashoua | |
| 6,294,383 B1 | 9/2001 | Isacson et al. | |
| 6,399,575 B1 | 6/2002 | Smith et al. | |
| 6,410,511 B1 * | 6/2002 | L'Italien et al. | 514/12 |
| 6,511,696 B1 * | 1/2003 | Gohman et al. | 426/601 |
| 6,541,452 B1 | 4/2003 | Hastings et al. | |
| 6,559,124 B1 | 5/2003 | O'Brien et al. | |
| 6,576,272 B1 | 6/2003 | Blechman | |
| 6,743,619 B1 * | 6/2004 | Tang et al. | 435/233 |
| 2002/0106436 A1 * | 8/2002 | Gohman et al. | 426/590 |
| 2002/0165266 A1 * | 11/2002 | Fishbein | 514/453 |
| 2003/0203372 A1 * | 10/2003 | Ward et al. | 435/6 |

FOREIGN PATENT DOCUMENTS

EP 1 325 747 7/2003

OTHER PUBLICATIONS

M.S. Harris, ed. Organ-meats-msg Jul. 25, 2001, [Internet document], accessed Nov. 30, 2005, 38 pages, <http://web.archive.org/web/20010725001910/http://www.florilegium.org/files/FOOD-MEATS/organ-meats-msg.text>.*
K.F. Sullivan, et al. J. Biol. Chem. 1986, 261(28), pp. 13317-13322.*
UniProt entry TBB_CHICK. accession No. P09206, 3 pages. accessed Nov. 30, 2005, sequence update Mar. 1, 1989.*
K. Bradsher. "Age-old recipe roils new Chinese Disney", Jun. 20, 2005, 2 pages.*
X. A. Alvarez et al., "Oral Cerebrolysin® enhances brain alpa activity and improves cognitive performance in elderly control subjects," *J. Neural. Transm.*, Suppl., vol. 59, pp. 315-328 (2000).
K. Bulloch et al., "Calcitonin Gene-Related Peptide Immunoreactivity in the Hippocampus and Its Relationship to Cellular Changes Following Exposure to Trimethyltin," *Journal of Neuroscience Research*, vol. 55, pp. 441-457 (1999).
L. Parnetti et al., "Posatirelin in the treatment of vascular dementia: a double-blind multicentre study vs placebo," *Acta Neurol. Scand.*, vol. 93, pp. 456-463 (1996).
M. Gonzalez-Gross et al., "Nutrition and cognitive impairment in the elderly," *British Journal of Nutrition*, vol. 86, pp. 313-321 (2001).
M. Yoshikawa et al., "Bioactive peptides derived from food proteins preventing lifestyle-related diseases," *BioFactors*, vol. 12, pp. 143-146 (2000).
Illana Gozes et al., "Peptides as Drug Candidates Against Alzheimer's Disease," *Drug Development Research*, vol. 56, pp. 475-481 (2002).
Wick, "Anti-aging medicine does it exist? A critical discuession of anti-aging health products," *Exp. Gerontol.*, vol. 37, pp. 1137-1140, 2002.
Ueki, "Drug of abuse," *Rinsho Byori*, vol. 50, No. 2, pp. 151-155, 2002.
Binstock, "The war on anti-aging medicine," *Gerontologist*, vol. 43, No. 1, pp. 4-14, 2003.

* cited by examiner

*Primary Examiner*—Cecilia J. Tsang
*Assistant Examiner*—Andrew D. Kosar
(74) *Attorney, Agent, or Firm*—Wenderoth, Lind & Ponack, L.L.P.

(57) ABSTRACT

The invention relates to a novel dietary supplement mixture having improved neuroprotective activity and preventing, ameliorating or counteracting neurodegeneration and preventing, counteracting and/or improving cognitive function decline. It also provides a dietary supplement, which is to be administered in an oral dosage form.

10 Claims, 8 Drawing Sheets

SEQUENCE LISTING

<160> NUMBER OF SEQ ID NOS: 2

<210> SEQ ID NO 1
<211> LENGTH: 7

```
-continued

<212> TYPE: PRT
<213> ORGANISM: ARTIFICIAL SEQUENCE
<220> FEATURE:
<223> OTHER INFORMATION: DESCRIPTION OF ARTIFICIAL SEQUENCE: SYNTHETIC
      CONSTRUCT

<400> SEQUENCE: 1

Asn Met Val Pro Phe Pro Arg
1               5

<210> SEQ ID NO 2
<211> LENGTH: 20
<212> TYPE: PRT
<213> ORGANISM: ARTIFICIAL SEQUENCE
<220> FEATURE:
<223> OTHER INFORMATION: DESCRIPTION OF ARTIFICIAL SEQUENCE: SYNTHETIC
      CONSTRUCT

<400> SEQUENCE: 2

Ala Ser Ala Phe Gln Gly Ile Gly Ser Thr His Trp Val Tyr Asp Gly
1               5                   10                  15

Val Gly Asn Ser
            20
```

NEUROPROTECTIVE DIETARY SUPPLEMENT

BACKGROUND OF THE INVENTION

The invention relates to a novel dietary supplement, which is useful as a neuroprotective agent and which is applied orally.

The number of old people is steadily growing worldwide. It is a fact that elderly people live longer nowadays. Therefore age-related deficiencies such as age-associated memory impairment, cognitive decline and the like are becoming an important public health problem.

DESCRIPTION OF THE RELATED ART

EP 1 325 747 A2 discloses a dietary supplement comprising balanced amounts of natural substances having neuroprotective acitivity, such as α-lipoic acid and γ-linoleic acid or soy-bean phospholipids in combination with compounds having anti-inflammatory and antioxidant and saccharo- and lipometabolism- regulating properties, together with complex B-vitamins.

SUMMARY OF THE INVENTION

It is an objective of the invention to provide a novel dietary supplement mixture having improved neuroprotective activity and preventing, ameliorating or counteracting neurodegeneration and preventing, counteracting and/or improving cognitive function decline.

Another objective of the invention is to provide a dietary supplement, which is to be administered in an oral dosage form.

DETAILED DESCRIPTION OF THE INVENTION

Figure 1:
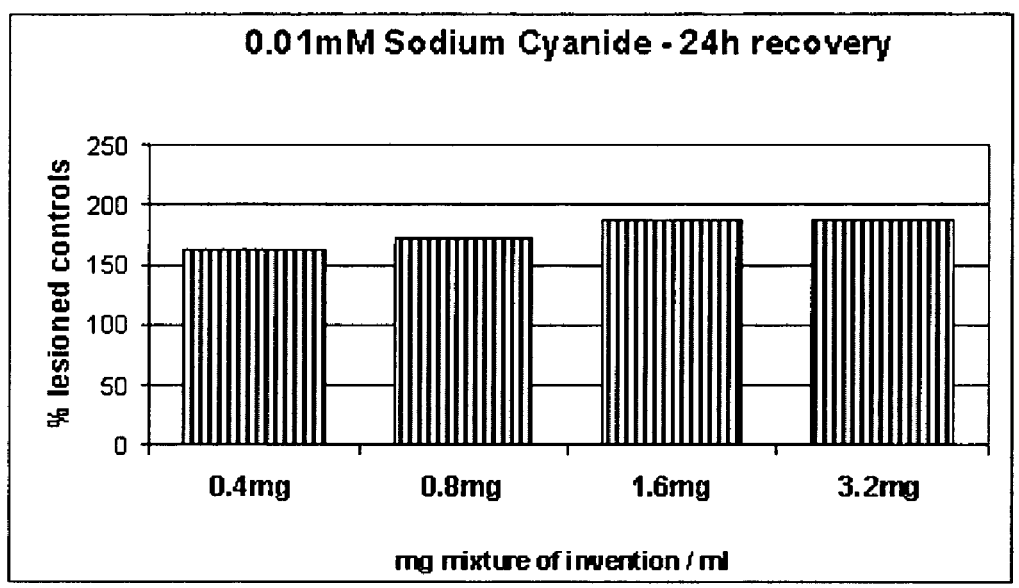
FIG. 1: Effects of different dosages of the invention on neuronal viability 24 h after cytotoxic hypoxia induced by exposure to Sodium-Cyanide.

The novel dietary supplement mixture having neuroprotective activity which comprises a peptide formulation, comprising at least one of the two peptides defined by sequence 1: NMVPFPR (SEQ ID NO: 1) or sequence 2: ASAFQGIGSTHWVYDGVGNS (SEQ ID NO: 2).

The novel dietary supplement mixture may prevent or ameliorate age-related neurodegeneration, age-related cognitive decline and age-related memory impairment. It serves as an agent to improve memory, attention and vigilance in humans, preferably in elderly humans.

The novel dietary supplement mixture consists essentially of molecules having a molecular weight of less than 10 kDa and comprises at least one of the peptides defined by the following sequences:

Sequence 1:  NMVPFPR              (SEQ ID NO: 1)

Sequence 2:  ASAFQGIGSTHWVYDGVGNS (SEQ ID NO: 2)

These peptides can be obtained by commonly known synthetic procedures. Sequence determination was performed by commonly known techniques such as mass spectrometry, tandem mass spectrometry, electrophoresis, chromatographic separation followed by sequencing and the like.

The novel dietary supplement mixture may further comprise additional peptides, having a molecular weight of less than 10 kDa.

It may further comprise amino acids.

Suitable amino acids are for example asparagine (N), methionine (M), glutamic acid (E), valine (V), proline (P), arginine (R), alanine (A), cysteine (C), phenylalanine (F), glutamine (Q), glycine (G), threonine (T), isoleucine (I), tryptophane (W), tyrosine (Y), threonine (T), serine (S), histidine (H), aspartic acid (D), lysine (K), leucine (L) and the like. The amino acids are preferably used in their optically active form, most preferably L-amino acids are used.

The novel dietary supplement mixture may further comprise vitamins, such as vitamin A, different vitamins of the B group, vitamin C, vitamin D, E and/or K. Further it may comprise mineral substances and/or trace elements such as calcium, magnesium, iron, copper, sodium, zinc, manganese, iodine, potassium, selenium, chromium, molybdenium, fluorine, chlorine, phosphorous. Further ingredients may be caffeine and taurine, fatty acids such as Ω-fatty acids, alpha lipoic acid, phospholipids, phosphatidylserines, plant extracts, such as ginkgo biloba, huperzine, precursors of neurotransmitters like DMAE (Dimethylaminoethanol) and the like.

It may further comprise flavouring substances, colorants like titaniumdioxide ferric oxides and the like, and/or preserving agents and the like. Preserving agents may be Ethylparaben (p-Hydroxybenzoic acid ethyl ester), Benzalkonium Chloride, Benzethonium Chloride, Benzoic acid, Butylparaben (p-Hydroxybenzoic acid butyl ester), Methylparaben (p-Hydroxybenzoic acid methyl ester), Potassium sorbate, Propionic acid, Propylparaben (p-Hydroxybenzoic acid propyl ester), Sodium benzoate, Sodium propionate, Sorbic acid and the like.

The mixture further may comprise acceptable additives, fillers and/or excipients such as microcrystalline cellulose, maltodextrine, magnesium stearate, colloidal silica, silicon dioxide, lactose, maltose, carboxymethylcellulose sodium, cellulose modified, vegetable cellulose, calcium phosphate, sodium phosphate, vegetable glycerine, sodium starch, polyvinylpyrrolidone, polyvinylpolypyrrolidone, cellulose gum, stearic acid, gelatine, mannitol, sodium ascorbate, glycerine, riceflour, maltodextrine dipotassium phosphate and the like.

Preferably the dietary supplement mixture of the invention comprises 10–30 wt % peptides, 2–20 wt % amino acids and up to 2–76 wt % additional ingredients, fillers and the like as defined above.

The dietary supplement mixture is applied orally in form of tablets, coated tablets, capsules, pastes, chewing tablets or drinking solutions. If a coated tablet is used the coating may be resistant against gastric juices, thus an enteric coated dosage form could be used. The dietary supplement mixture may in its oral dosage form be applied at least one time daily.

The dietary supplement product of the invention is useful to prevent, ameloriate, counteract deficiencies related with the aging process preferably in mammals, especially in humans, most preferably in elderly humans.

It may be used as an agent to protect neurons against metabolic deficits and stress associated with aging processes, to prevent, counteract and/or ameliorate the consequences of age-related neuronal lesions due to hypoxia or ischaemia consequences, of age-related neuronal lesions due to intracellular calcium overload, the consequences of age-related neuronal lesions induced by e.g. L-glutamate and the consequences of age-related neuronal lesions due to oxidative stress.

It is particularly also useful to prevent, counteract and/or ameliorate the consequences of age-associated neurodegeneration, to prevent neuronal cell death due to cell stress, neurodegenerative events and intoxication, to maintain and preserve normal neuronal cytoarchitecture during aging processes, to support and/or improve synaptic function and synaptic density, to prevent, counteract, and or ameliorate the consequences of the age-related decline of synaptic plasticity and of synaptic density, processes, to activate cerebral mechanisms related to attention and memory performance, to prevent, counteract, and/or improve cognitive function decline, to prevent, counteract, and/or improve memory function decline, to prevent, counteract, and/or improve attention deficits, to prevent, counteract, and/or improve a decrease of vigilance associated with aging processes and to support, maintain and/or improve long term memory and procedural memory as well as learning performance, attention and vigilance, and to preserve/support healthy mental function during the aging processes.

EXAMPLE 1

Preparation of a Powder Mixture:
   49.490 kg Powder comprising 23.0% peptides, 8.8% amino acids and 68.2% lactose
   6.738 kg Carboxymethylcellulose
   9.607 kg microcrystalline cellulose
   0.525 kg colloidal anhydrous silica were sieved through a 1.2 mm sieving screen into a stainless steel drum and mixed with a tumble type mixer at a mixer speed of 6 rpm for 10 minutes (mixture 1). 1.015 kg magnesium stearate were sieved through a 1.2 mm sieving screen into a stainless steel drum containing mixture 1. Subsequently, the whole granulate was mixed with a tumble type mixer at a mixer speed of 4 rpm for 5 minutes (final mixture).

Compression of the Powder Mixture (Tabletting)

The final mixture was pressed with a tablet press with a tabletting speed of about 40,000 tablets per hour into tablets with an average weight of 385 mg. A round, double-sided convex punch shape with a diameter of 11 mm was used.

Thus tablets with the following properties were obtained:

| | |
|---|---|
| average weight: | 385.0 +/− 7.7 mg |
| hardness: | 40–70 N |
| disintegration: | not more than 15.00 minutes |
| friability: | not more than 1.00% |

(All test methods according to Ph.Eur.)

EXAMPLE 2

Coating of Tablets

The tablets obtained in example 1 may be coated.

The following ingredients were mixed with a propeller mixer to form a film-coating suspension:
   23.810 kg Cellulose acetate phthalate (30% aqueous solution)
   0.595 kg talc
   0.833 kg titanium dioxide
   1.429 kg triethyl citrate Tablets were coated with film-coating suspension to a final weight of 428.0 mg per film tablet in a drum coater.

The coated tablets can be glossed with wax or paraffin.

Thus film-coated white tablets with the following parameters were obtained:

| | |
|---|---|
| average weight: | 428.0 +/− 8.6 mg |
| disintegration: | not more than 30.00 minutes |
| friability: | not more than 1.00% |

(All test methods according to Ph.Eur.)

EXAMPLE 3

The powder mixture used for tabletting (see example 1) can alternatively be filled into hardgelatine capsules.

Hardgelatin capsules of size #0 or #1 were filled with 385 mg of the powder mixture. Thus capsules with the following parameters have been obtained:

| | |
|---|---|
| average weight: | 462.0 +/− 28.8 mg (size 1) |
| average weight: | 481.0 +/− 28.8 mg (size 0) |
| disintegration: | not more than 15.00 minutes |

EXAMPLE 4

Preparation of a drink solution:
   70.72 g Powder comprising 23.0% peptides, 8.8% amino acids and 68.2% lactose
   400.00 g Saccharose
   5.00 g Benzoic acid were dissolved in 1500 g water in a glass flask equipped with a propeller mixer. An almost clear solution is formed (solution 1).

85.0 mg Riboflavine
17.00 g Strawberry essence or 2.6 g Flavour Orange
10.00 g Flavour Milk-caramel were dissolved in solution 1 in a glass flask equipped with a propeller mixer. An almost clear, yellow solution is formed (solution 2).

125.0 mg Vitamine E was suspended in 200.00 g water in a glass flask equipped with a propeller mixer. This suspension was added to solution 2 (solution 3).

5.00 g Sodium alginate is dissolved in 500.00 g water with temperature between 40° C. and 50° C. and added to solution 3 (solution 4).

Solution 4 was filled up to 5000 ml with water and mixed in a glass flask equipped with a propeller mixer. An almost clear, yellow solution is formed which is further clarified by filtration through a 0.45 µm membrane filter. The solution is filled into 20 ml glass bottles with plastic screw caps.

EXAMPLE 5

Neuroprotective Effect—Protection of Cortical Neurons in Culture Against Different Age Associated Lesions 5.1. Methods All items necessary were sterilized prior to the experiments. Stock solutions were purchased already sterile and final solutions were mixed in the laminar airflow cabinet.

The culture medium for the lesion assays consists of Dulbecco's modified Eagle's medium (DMEM) with 4.5 g glucose/l, 5% foetal calf serum, 0.01% gentamycin and 2 mM L-glutamine. L-glutamine in the medium is required for growth and differentiation, and gentamycin has to be added to prevent cell cultures from an infection with mycoplasm or other unwanted microorganism. For each experiment the nutrition medium was freshly prepared in the laminar air flow cabinet under sterile conditions.

The cells used for the experiments were Lohman Brown chicken embryo hybrids. One-day-old fertilized eggs are purchased from a local chicken breeder (Schlierbach Geflue-gel GmbH, Austria) and stored in the lab under appropriate conditions (12±0.3° C. and 80±5% humidity). At embryonic day 0 eggs are transferred into a breeding incubator and stored under permanent turning until embryonic day 8 at 38±0.5° C. and 55±5% humidity. For isolation of neurons 3 to 4 chicken embryos are used per experiment. The age of the embryos is very critical, since only in a particular period of development the brain almost exclusively contains nerve cells and less than 5% glia (Pettmann, B., Louis, J. C. and Sensenbrenner, L M. (1979) *Nature* 281:378–380).

The eggs were wiped with 70% ethanol and cracked with large forceps at the blunt end. After decapitation of the embryo, the tissue covering the telencephalon was removed and hemispheres were collected. After removing any lease tissue and remaining meningeal membranes, hemispheres were transferred into a dish containing nutrition medium. Thereafter the tissue was dissociated mechanically by using a 1 ml pipette and by squeezing 3 times through a sterile nylon sieve with a pore size of 100 µm.

Using a standard trypan blue dye exclusion test (PM Laboratories) the number of cells and the cell viability can be determined. For cell counting one part of the cell suspension has to be diluted with 9 parts of trypan blue solution (270IJ I PBS and 180IJI 0.5% trypan blue solution). Living cells and blue stained death cells are counted in a Buerker-Tuerk-hemocytometer. The total number of cells minus the stained dead ones gives the amount of vital cells.

For the lesion assays the original tissue culture medium was removed from the cells and stored. New medium containing e.g. sodium cyanide or cholchicine (sodium cyanide 0.01 mM; 0.1 mM; 1 mM; cholchicine 0.1 µM; 1 µM; 10 µM) was added and remained with the cells for 30 minutes. Then the lesion medium was removed and discarded, the original culture medium was replaced and the culture was maintained for further 24 or 48 hours of recovery period. Thereafter the viability assay was performed.

In the experiments described Poly-D-Lysin coated 96-well microtiter plates were used. 80 µl medium containing $6 \times 10^5$ cells/ml were added to each well of the previously prepared microtiter plates already containing 80 µl substance-supplemented-medium. Therefore, the final amount of cells in each well is $3 \times 10^5$/ml nutrition medium. Lesioned and unlesioned controls were grown in nutrition medium only during the whole experiment. When preparing plates; routinely outside wells are filled with nutrition medium only to prevent evaporation. Plates are kept at 37° C., 95% humidity and 5% $CO_2$ without change of media until end of the experiment. Neurons begin to extend processes after a few hours in culture.

The mixture according to the invention was used as a ready to use solution in ampoules. To achieve concentrations of 1.25, 2.5, 5, 10, 20, 40, 80, 160 µl/ml medium the mixture was added to the wells once in the appropriate concentrations at DIV (=days in vitro) 1 and remained with the neurons until the end of the experiment. Lesion started at DIV 8, evaluation of cell viability was performed on DIV 9 and DIV 10, respectively. During the remaining culture period after the lesion was performed no further substance was added.

In the lesion assays the mixture of the invention was tested under identical conditions on two different days. In every experiment at least 6 particular values were generated for lesioned and unlesioned controls and 2 for each concentration (in total n=12). The mixture of the invention was supplemented in concentrations of 1.25, 2.5, 5, 10, 20, 40, 80, 160 µl/ml medium. Different experimental groups with different lesions were investigated.

At the end of each experiment the viability of remaining nerve cells was measured with a colorimetric MTT-reduction assay. This assay is based on the reduction of yellow MTT (3-(4,5-dimethylthiazol-2-yl)-2,5,diphenyl tetrazolium bromide), to dark blue Formazan crystals by mitochondrial dehydrogenases (succinate dehydrogenase). Since the described reaction is catalysed in living cells only the assay can be used for the quantification of cell viability. For the determination of cell viability MTT solution was added to each well in a final concentration of 0.5 mg/ml. After 2 h the MTT containing medium was aspired. Cells were lysed with 3% SDS, Formazan crystals dissolved in Isopropanol/HCl. To estimate optical density a plate reader (Anthos HT II) was used (570 nm). Neuronal viability is expressed in optical density (OD).

For analysis descriptive statistical methods were used. MTT values (ODs) are expressed as mean±standard deviation.

5.2. Results

At first different concentrations of the lesioning compounds (sodium cyanide and colchicine) have been used to achieve a neuronal damage of approximately 50% compared to unlesioned neurons. Appropriate lesioning dosages and lesion time has been chosen in the way that the overall damage is significant but still allows neurons to survive and to recover. Too high dosages are leading to rapid neuronal death limiting the possibility of neuroprotective substances to rescue them; too low dosages are also not allowing a reliable assessment of protective compounds because the difference between lesioned and unlesioned controls is too low.

Figure 2:
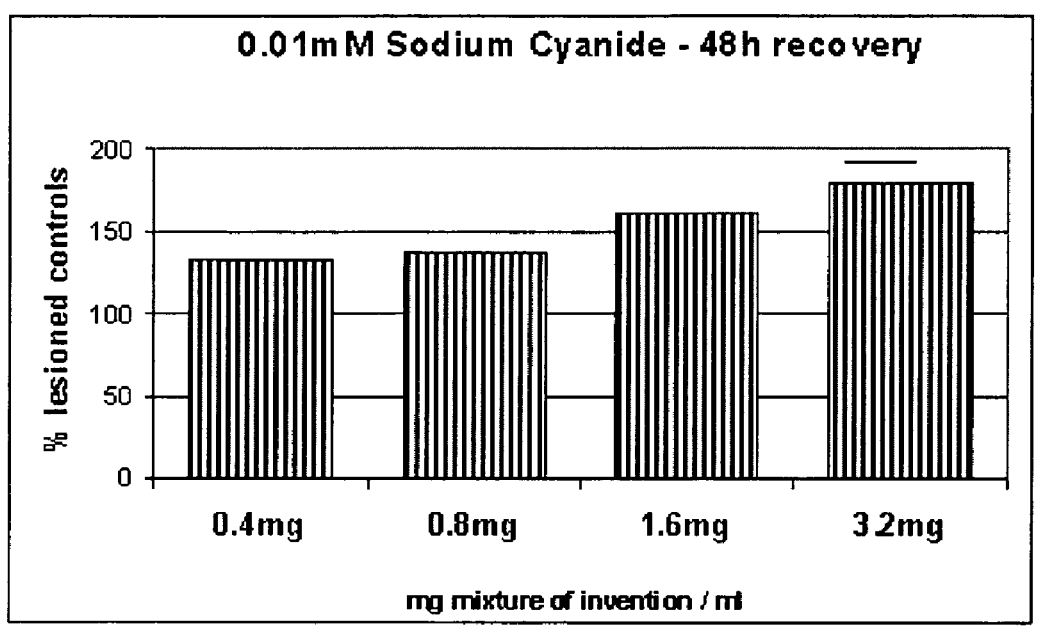
FIG. 2: Effects of different dosages of the invention on neuronal viability 48 h after cytotoxic hypoxia induced by exposure to Sodium-Cyanide.
Figure 3:
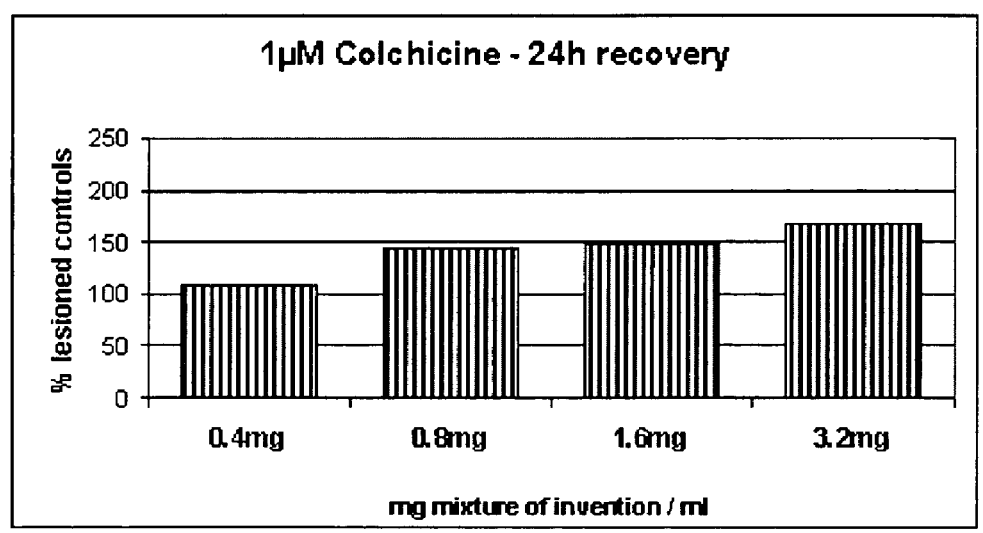
FIG. 3: Effects of different dosages of the invention on neuronal viability 24 h after cytoskeletal disruption induced by exposure to colchicine.
Figure 4:
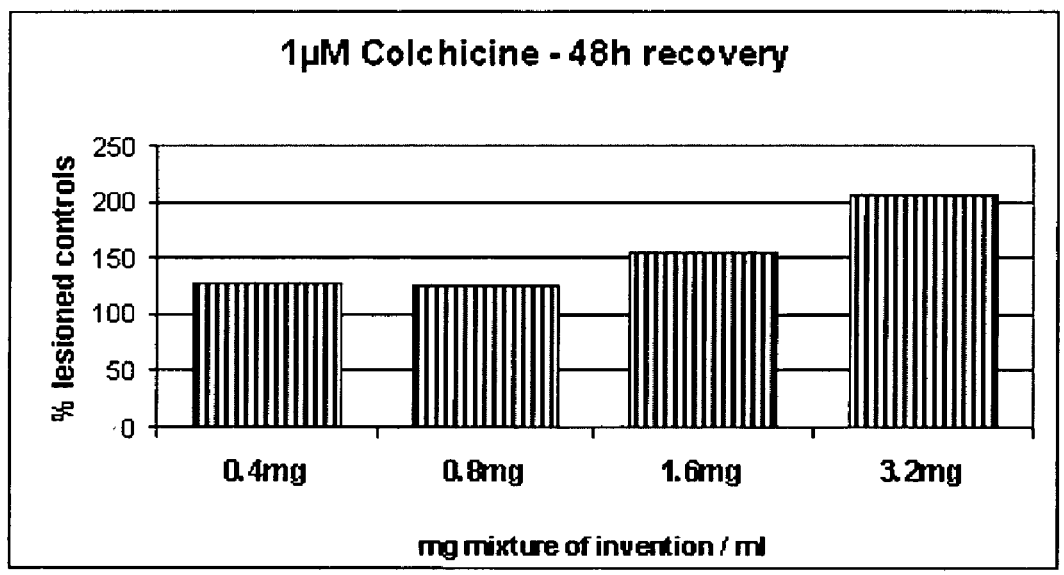
FIG. 4: Effects of different dosages of the invention on neuronal viability 48 h after cytoskeletal disruption induced by exposure to colchicine.

The evaluation of cell viability 48 hours after the 30 minutes of sodium cyanide intoxication shows still a significant neuroprotective effect of the invention, but to a little bit lower extent than observed after 24 hours (FIGS. 1 and 2). Cytoskeletal disruption by colchicine leads also to massive neurodegeneration. After 24 hours the low dosage of 0.4 mg of the invention is not able to display a significant rescue, but all other dosages are increasing neuronal viability by approximately 50% above the level of lesioned controls. 48 hours after onset of lesion all dosages are having a clear neuroprotective effect, and now viability in the high dose group of 3.2 mg is already 100% above viability of unlesioned controls, indicating that the majority of neurons can be rescued (FIGS. 3 and 4).

FIGS. 1–4 represent relative changes in viability due to the application of the mixture of the invention in comparison to untreated lesioned controls (=100%):

FIG. 1 shows the effects of different dosages of the invention on neuronal viability 24 hours after cytotoxic hypoxia induced by exposure to Sodium-Cyanide.

FIG. 2 shows the effects of different dosages of the invention on neuronal viability 48 hours after cytotoxic hypoxia induced by exposure to Sodium-Cyanide.

FIG. 3 shows the effects of of different dosages of the invention on neuronal viability 24 hours after cytoskeletal disruption induced by exposure to colchicine.

FIG. 4 shows the effects of different dosages of the invention on neuronal viability 48 hours after cytoskeletal disruption induced by exposure to colchicine.

The overall conclusion from these experiments clearly demonstrate that the invention is able to keep nerve cells alive, protect them from metabolic stress and failures and stimulate cell viability, the outgrowth of neuritic processes and their branches. If the neuronal damage induced by the different toxins in vitro is too severe only slight protection can be achieved, in case of mild to moderate lesion condition pronounced dose dependent effects could be evaluated.

However, the complex composition of the invention suggests that the peptides are acting in a synergistic way, combining neurotrophic stimulation, increased synthesis of anti-apoptotic factors and structural proteins, inhibition of abnormally up regulated proteases and metabolic regulations. The summary of the effects show an interesting potency of this dietary supplement to protect highly vulnerable cells in vitro.

EXAMPLE 6

Long Term Treatment of Aged Rats (3 Months Daily Treatment by Oral Gavage in Comparison to Oral Application of Physiological Saline 6.1. Methods 6.1.1. Treatment and Behavioral Tests All experiments were performed in 18-month-old (±1 month old) Long Evans rats. The rats were randomly designed to the different groups, either treated with mixture oft the invention or with physiological saline as control. The number of animals per group was between 12 and 15. Animals in both experimental groups were treated over a period of 3 months with 1 daily oral gavage of either the mixture oft the invention as defined in example 5 or saline. During the last 4 treatment days of each month (treatment day 27 to 30=trial day 1–4; treatment day 56–60=trial day 5–8 and treatment day 87 to 90=trial day 9–12) behavioral tests in the MWM (Morris water maze: learning task specifically challenging hippocampal contribution to spatial orientation and learning) were performed to evaluate learning and memory function of the animals.

The used MWM consists of a round swimming pool with a diameter of 170 centimeters and a height of 45 centimeters. An additional inner aluminum ring served to hide all cables connecting the computer system to the hidden platform. This is necessary not to provide the animals with inter-maze marks which would influence the normal learning behavior. The inner surface of the pool is painted black so that the transparent Plexiglas platform can not be detected from outside. The submerged platform (diameter 15 centimeters) was always located at the exactly same position in the pool, the south-east quadrant. The swimming trail of each rat was detected using a light emitting diode which signals were detected by a video camera attached to a personal computer to enable continuous tracking of the swimming path. Specifically designed software (ART3) allows calculation of length of swimming path, latency to reach the hidden platform, time spend in quadrants, passages over the target area and all other parameters suitable for assessment of learning and memory function. Escape Latency for finding the platform as well as the length of the swimming path was used for statistical calculations about the effects of mixture oft the invention on learning function. Each animal performed 4 swimming trials on each trial (training) day. Statistical analysis was performed using the h-test according to Kruskal and Wallis or in case of normally distributed values using ANOVA and the Scheffe test for post hoc analysis.

6.1.2. Histological Examinations

Immediately after finishing the behavioral experiments in the MWM 4 to 6 rats of each group were sacrificed by an overdose of Nembutal. For proper histological preparation transcardial perfusion with physiological saline and formalin was performed. For complete fixation the brains were transferred into 10% formalin and later on imbedded into paraffin. Slices of 3 µm (Bregma Level~–4.00 mm) thickness were cut on the microtome and incubated with an antibody against the vesicular protein synaptophysin. The immunoreaction was visualized using an enzyme reaction (APC-method, peroxidase conjugated secondary antibody, diaminobenzidine was used as substrate).

Due to the fact that there is a good correlation between synaptic density and synaptophysin immunoreactivity a light microscopic quantification of synaptic counts using an image analyzing system (LUCIA-Nikon Photo Systems, AUSTRIA) was done. Image analyzing was performed in clearly defined sub areas of the hippocampus (CA1 stratum radiatum, CA2 stratum radiatum, CA3 stratum radiatum, CA3 stratum lucidum, dentate gyrus lateral blade and dentate gyrus medial blade) as well as in the entorhinal cortex (layers 2 and 3). For this purpose the number of synaptophysin immunoreacitve dots and the complete area of the dots was measured and statistically calculated (Kruskal-Wallis ANOVA).

6.2. Results

6.2.1. Behavioral Tests in the MWM

Escape Latency

The Escape Latency is defined as time between placing the animal into the swimming pool and successfully finding the hidden platform in the MWM. Animals have to get orientated using extra maze landmarks as described before. The Escape Latency is a measure for learning and memory.

During the first training course after 1 month of application no significant difference between both experimental groups could be detected. However there is a clear tendency that the mixture of the invention treated rats are acquiring the task faster, but after 4 days of training the result is identical.

At the end of the second month there is a statistically significant difference between the mixture oft the invention group and the saline treated controls on the first training day (p=0.0049). This indicates stabilization of long-term memory and most-likely also an improved procedural learning. With the mixture of the invention treated rats remember the original platform position from the first trial onwards, with other words they have not forgotten the position within the time period of one month and because they know already about the procedure of the task they perform better than the controls. Because they show very low Escape Latency already on the first training day at the end of the second month further improvement is not possible because of a ceiling effect due to limits in swimming speed. The control animals show a continuous improvement from training day to training day but on the last day they are still worse than the mixture oft the invention treated animals. At end of the 3 months treatment period the mixture oft the invention treated rats still start with lower latencies than the control group. However both groups show very good performance and there is no further room for improvement.

Investigation on Long Term Memory

Analysis of Differences in Escape Latency Between Day 4 Trial 4 and Day 5 Trial 1 as Well as Day 8 Trial 4 and Day 9 Trial 1:

The evaluation of long-term memory (difference in latency between the last trial of the last testing day at end of the first month and the first trial of the first training day at the end of month 2; difference between the last trial of training day at the end of month 2 and the first trial of the first training day at the end of the 3 months treatment period) shows the clear tendency of an improved long term memory in mixture oft the invention treated rats. The mixture of the invention treated animals improve in their performance by almost 10 seconds if the Escape Latency of the last trial on the last training day of the first month is compared to the Latency of the first trial on the first training day at the 2 months period. In contrast the control animals are slightly slower. Comparing the performance between the last trial on last training day end of the 2 months period to the first trial at the first training day after end of the treatment period again shows an improvement of more than 10 seconds in favour of the mixture oft the invention group. The saline treated controls almost show no change, what indicates that the long-term memory in the mixture oft the invention treated rats is improved.

Analysis of the Escape Latency Between the First Training Day after One Month Period and the First Training Day after 2 Months of Treatment and the First Training Day after 3 Months Treatment Period Respectively As a second measure for long-term memory the differences between the very first learning day to the first training days after 2 months and 3 months of treatment have been evaluated. This should serve as a measure of total improvement in Escape Latency comparing the naive situation to the situation of re-training. Greater differences reflect better long-term memory; small differences indicate that the animals forgot the platform location during the treatment period without training.

Figure 5:
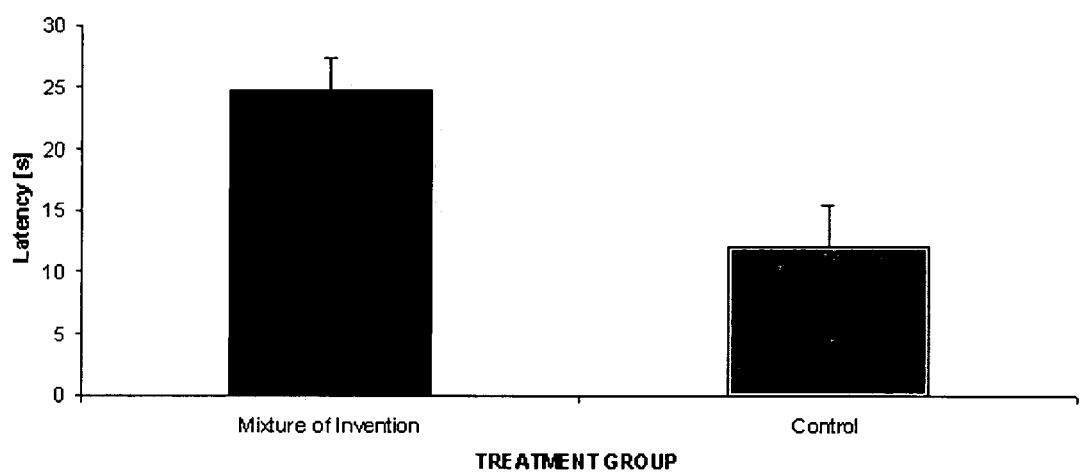
FIG. 5: Differences in Escape Latencies between Day 1 and Day 5.

FIG. 5 (Differences in Escape Latencies between training Day 1 (1 month treatment) and Day 5 (2 months treatment); Data represent mean±SEM. **=P<0.01) demonstrates the differences between the very first training day, where the naive rats were put first time to the MWM and the re-training after 2 months of treatment. The mixture oft the invention treated animals improved by almost 25 seconds or nearly 50% compared to the first training day, whereas the saline treated controls only showed an improvement of roughly 12 seconds or less than 25%. The comparison in differences of Escape Latency between first training day and re-training on the first learning day after end of the treatment period (3 months) does not show any significant differences between the groups. There is still a trend in favour of the mixture oft the invention treatment, but the data clearly indicate that repetition of training finally leads to success in all treatment groups. We have to consider that all experiments have been performed in old, but otherwise healthy animals without any obvious neurological disturbances. Therefore it was expected that prolonged training will continuously increase the cognitive performance in both treatment arms.

Evaluation of Length of Swimming Path

The Escape Latency can be biased by motoric differences and therefore also the length of the swimming path was calculated. Increased swimming speed or diminished swimming speed would mimic otherwise changes in learning and memory. The length of the swimming trail is an independent measure of learning and memory performance independent from swimming speed.

The data confirm the statistical significant difference between mixture oft the invention treated rats and controls on the first training day after end of the 2 month treatment period. (p=0.0133). This indicates that the previously analyzed data are consistent and that mixture oft the invention treatment is improving the cognitive performance independent from any changes in motoric behavior (FIG. 6).

Figure 6:
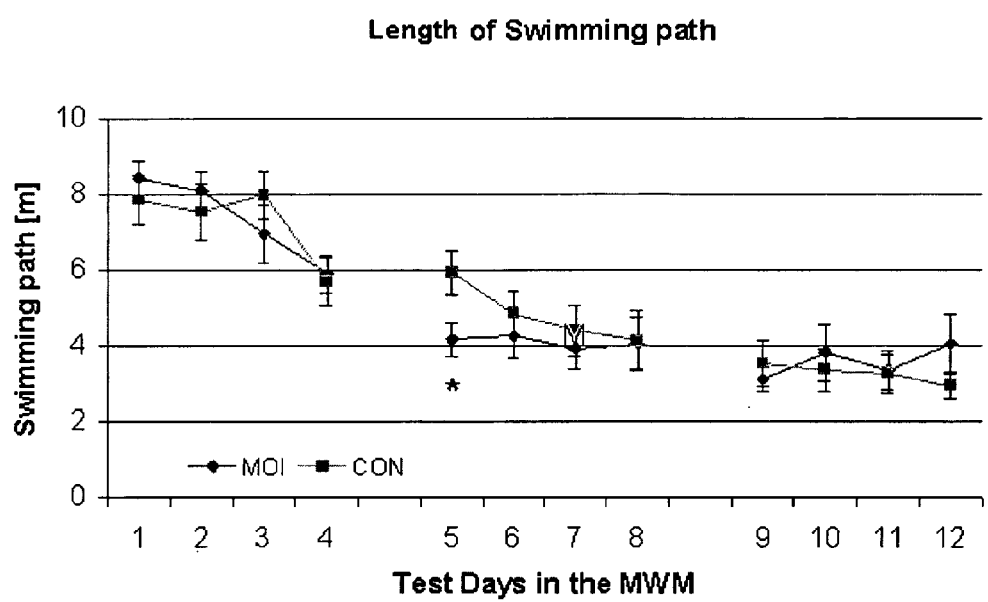
FIG. 6: Length of swimming path in the Morris water maze on test days 1–4, 5–8 und 9–12. Data represent mean±SEM. *=P<0.01 [MOI=mixture of invention; con=control].

FIG. 6 shows the length of swimming path in the Morris water maze on test days 1–4, 5–8 und 9–12. Data represent mean±SEM. *=P<0.01 [MOI=mixture of invention; con=control]

Analysis of Differences in Length of Swimming Path Between Day 4 Trial 4 and Day 5 Trial 1 as Well as Day 8 Trial 4 and Day 9 Trial 1:

The comparison of the length of swimming path between the last trial in the first series of training sessions and the first trial in the second training session after 2 months of treatment reflects exactly what has been seen at the evaluation of the Escape Latencies. The length of swimming path is approximately 2.1 meter shorter in the mixture oft the invention treated group what means that they navigate more exactly even after 4 weeks without training. The controls need 1.4 meter longer to find the platform reflecting some degree of difficulties in initial retrieval, or with other words they have to re-learn the exact and shortest direction to the target.

The length of the swimming path is almost 2 meters shorter if we compare the performance of the last training trial of the last test day of the second course (after 2 months of treatment) to the performance on the first trial at the first training day at the end of the 3 months period. This again indicates a strong influence of mixture of the invention on long term memory function. The control animals do not show any further improvement.

6.2.2. Histological Evaluation of Synaptic Density

Number of Synaptophysin Immunoreactive "Dots"

Figure 7:
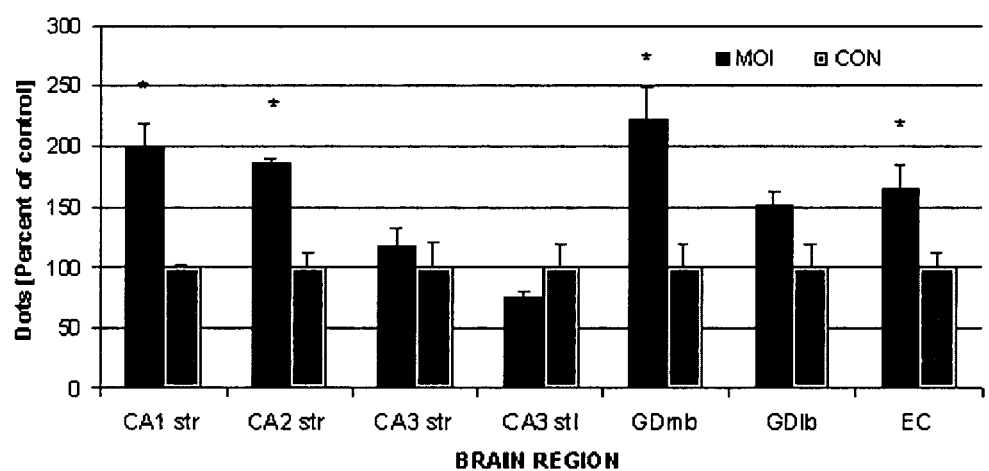
FIG. 7: Area of synaptophysin immunoreactivity in different regions of the hippocampal formation in percent of control values. 100%=immunoreactive dots counted in the saline control group. Bars are representing the mean±SEM. *=P<0.05 [MOI=mixture of invention; CON=control].

The 3 months treatment course with mixture oft the invention leads to a statistically significant increase of synaptic density in 4 out of the investigated areas (FIG. 7). In the CA3 stratum radiatum and in the dentate gyrus lateral blade there is at least a strong trend towards increase synaptic density in the mixture oft the invention treated animals, and only in the CA3 stratum lucidum the treatment does not result in increased synaptic density.

Evaluation of the Area of Synaptophysin Immunoreactivity

In contrast to the previous evaluation where every single immunoreactive dot was counted now the overall area covered by synaptophysin immunoreactivity was measured in comparison to the overall area of the brain slice after correction for blood vessels and tissue disruption. The result reflects data obtained with counting of immunoreacitve dots, the only exception that the effects in the entorhinal cortex are slightly below the level of significance. (p=0.0550). All other differences remain to be significant and the general trend of increased synaptic density in the mixture oft the invention treated rats could be confirmed.

FIG. 7 shows the area of synaptophysin immunoreactivity in different regions of the hippocampal formation in percent of control values. 100%=immunoreactive dots counted in the saline control group. Bars are representing the mean±SEM. *=P<0.05 [MOI=mixture of invention; CON=control]

The results of the behavioral tests in the Morris water maze show from the end of the second month a statistically significant difference between the mixture of invention treated group and the control group. The animals treated with mixture of invention find the hidden platform in the Morris water maze faster than the control group. This shows that the mixture of invention improve long term memory in healthy old aged rats. The data suggest that long term ingestion of growth factor like peptides is well tolerated and is able to provide neurotrophic stimulation to the brain. The improved cognitive performance with mixture of invention shown in this experiments correlates with morphological changes in the hippocampus. In summary, the invention constitutes a novel supplement which may help to maintain memory and learning performance during aging and might reduce the risk of cognitive function loss associated with the aging process.

EXAMPLE 7

Cognitive Function Enhancement in Healthy Elderly Humans 7.1. Methods

Six healthy adult people (4 women and 2 men), age 63.0+/−3.6 years (range: 51–76 years), were included in this study. Weight, height, BMI (body mass index) and other biological characteristics of the sample were recorded.

Medical and psychometric evaluations, quantitative EEG and ECG as well as laboratory analysis were performed in all subjects before inclusion. None of the subjects met DSM-IV and/or NINCDS-ADRDA criteria for senile dementia (American Psychiatric Association, 1994; McKhann et al., 1984). All subjects were completely drug-free before and during the study. Written informed consent was obtained from all study participants. The study was by the Institutional Review Board and conducted according to Good Clinical Practice guidelines.

The study was an open-label, exploratory trial aimed to evaluate the effects of mixture oft the invention, administered orally and in a single dose, on brain functioning in healthy elderly people. A total of six subjects older than 50 years were included. The duration of the study for each participant was of 2 days. Participants underwent cognitive assessment on day 1, 24 h before administration of mixture oft the invention and a second, post-treatment evaluation on day 2, 6 hours after administration of mixture oft the invention. All study participants received a single oral dose of mixture of the invention (180 mg).

7.2. Results

Average MMSE score at baseline was 28.4±0.4 points for the studied subjects. A significant improvement (FIG. 8) in ADAS-memory scores was observed after treatment with mixture oft the invention (6.9±1.0 omissions at baseline versus 4.9±1.0 omissions after treatment; p<0.01). This memory improvement was also statistically significant for the word recognition item (2.8±0.6 omissions vs 1.5±0.7 omissions; p<0.05).

Figure 8:
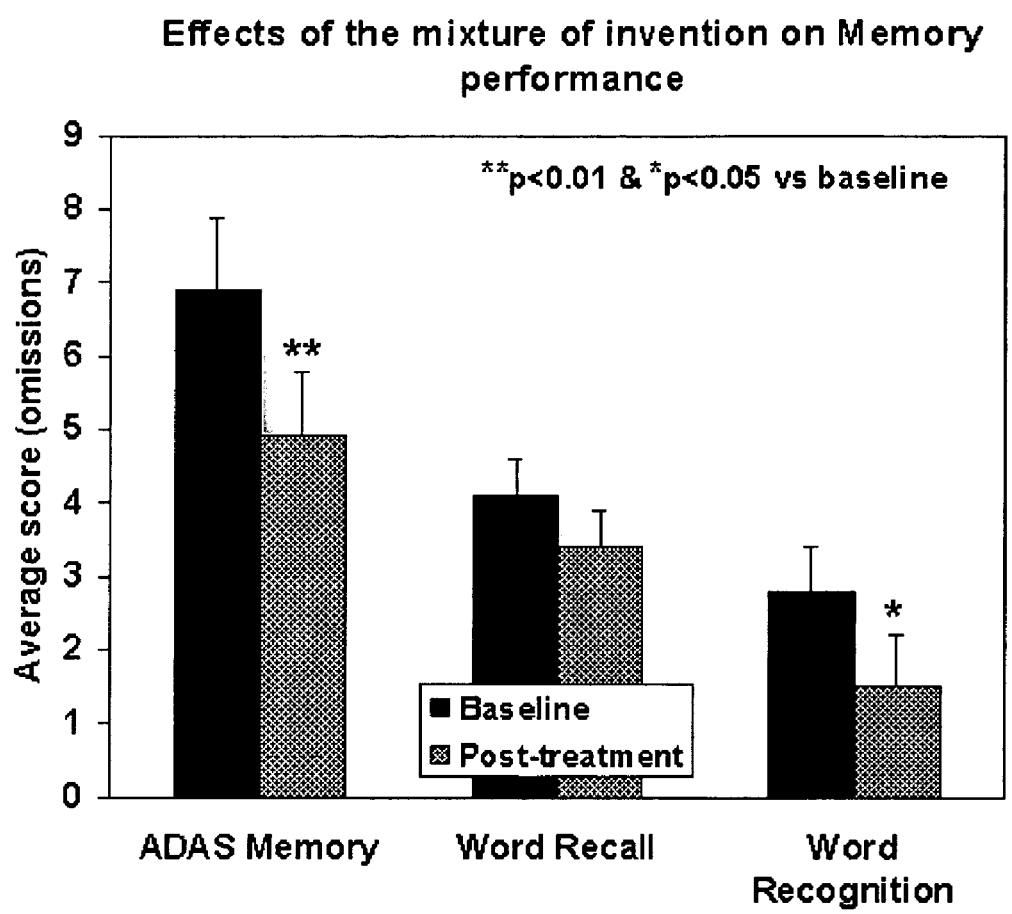
FIG. 8: Effects of the invention on memory performance, evaluated by using the memory items of the ADAS, in healthy elderly subjects. ADAS memory scores (omissions) represent the sum of the Word Recall and Word Recognition items.

FIG. 8 shows the effects of the invention on memory performance, evaluated by using the memory items of the ADAS, in healthy elderly subjects. ADAS memory scores (omissions) represent the sum of the Word Recall and Word Recognition items According to the results of this study, the mixture of the invention supports and improves memory performance in healthy elderly subjects after the administration of a single dose. The improvement induced by the mixture of the invention reached significant values in the word recognition task and in the total memory subscore of the ADAS, but not in the word recall item. The mixture of the invention also enhances, in a nonsignificant manner, performance in cognitive tasks of the SKT related to both, attention and memory performance. Individual SKT tasks where best effects after the treatment with the mixture of the invention were seen included the items arranging blocks, counting symbols and recognition memory. These effects indicate that the invention might potentiate attention and memory functions in adult-elderly people without cognitive impairment.

The present results indicate that the mixture of the invention supports brain functioning in healthy elderly volunteers, with clearly positive effects on cognitive performance (memory and attention). Accordingly the mixture of the invention seems to constitute a useful dietary supplement to support and improve cognitive performance and attention in elderly subjects.

What we claimed is:

1. A dietary supplement mixture having neuroprotective activity which comprises a peptide formulation, comprising at least one of a peptide consisting of the amino acid sequence of NMVPFPR (SEQ ID NO: 1) or a peptide consisting of the amino acid sequence of ASAFQGIGSTH-WVYDGVGNS (SEQ ID NO: 2).

2. The dietary supplement mixture according to claim 1 further comprising additional amino acids.

3. The dietary supplement mixture according to claim 1 further comprising peptides with a molecular weight less than 10 kDa.

4. The dietary supplement mixture according to claim 1 further comprising trace elements and/or mineral substances and/or vitamins and/or caffeine and/or taurine and/or fatty acids and/or phospholipids, and/or phosphatidylserines and/or plant extracts.

5. The dietary supplement mixture according to claim 1 further comprising acceptable additives and/or excipients and/or fillers and/or colouring substances and/or flavouring substances.

6. An oral dosage form comprising a dietary supplement mixture according to claim 1 and acceptable additives and/or excipients and/or fillers and/or colouring substances and/or flavouring substances and/or solvents.

7. The oral dosage form comprising a dietary supplement mixture according to claim 6, wherein the total peptide concentration is 2–20 wt %.

8. The oral dosage form according to claim 7 further comprising 10–30 wt % amino acids.

9. A method of treating age-associated memory impairment and/or age-associated cognitive decline and/or benign senescent forgetfulness, which comprises administering to a patient in need thereof an effective amount of the dietary supplement mixture according to claim 1.

10. A method of supporting healthy mental function during the aging processes, which comprises administering to a patient in need thereof an effective amount of the dietary supplement mixture according to claim 1.

* * * * *